US008238513B2

(12) United States Patent
Ma

(10) Patent No.: US 8,238,513 B2
(45) Date of Patent: Aug. 7, 2012

(54) IMAGING SYSTEM AND METHOD UTILIZING PRIMARY RADIATION

(76) Inventor: Feng Ma, Morrisville, NC (US)

( * ) Notice: Subject to any disclaimer, the term of this patent is extended or adjusted under 35 U.S.C. 154(b) by 1145 days.

(21) Appl. No.: 12/067,383

(22) PCT Filed: Sep. 19, 2006

(86) PCT No.: PCT/US2006/036550
§ 371 (c)(1),
(2), (4) Date: Mar. 19, 2008

(87) PCT Pub. No.: WO2007/035775
PCT Pub. Date: Mar. 29, 2007

(65) Prior Publication Data
US 2009/0016593 A1    Jan. 15, 2009

Related U.S. Application Data

(60) Provisional application No. 60/596,348, filed on Sep. 19, 2005.

(51) Int. Cl.
*A61B 6/00* (2006.01)
(52) U.S. Cl. ............................... 378/6; 378/86; 382/131
(58) Field of Classification Search .................. 382/131, 382/132; 378/6, 7, 86
See application file for complete search history.

(56) References Cited

U.S. PATENT DOCUMENTS

| 4,896,343 | A | * | 1/1990 | Saunders | 378/95 |
| 6,163,589 | A | * | 12/2000 | Vartanian | 378/7 |
| 6,320,933 | B1 | * | 11/2001 | Grodzins et al. | 378/89 |
| 6,714,620 | B2 | * | 3/2004 | Caflisch et al. | 378/65 |
| 7,609,803 | B2 | * | 10/2009 | Okamoto et al. | 378/7 |
| 7,907,697 | B2 | * | 3/2011 | Maltz | 378/7 |
| 8,121,249 | B2 | * | 2/2012 | Wang et al. | 378/6 |
| 2001/0036250 | A1 | * | 11/2001 | Hartick et al. | 378/147 |
| 2002/0048339 | A1 | * | 4/2002 | Schneider et al. | 378/7 |
| 2002/0048347 | A1 | * | 4/2002 | Saito | 378/207 |
| 2003/0099329 | A1 | * | 5/2003 | Schotland et al. | 378/210 |
| 2004/0091079 | A1 | * | 5/2004 | Zapalac | 378/86 |
| 2004/0161073 | A1 | * | 8/2004 | Nokita | 378/4 |
| 2004/0202360 | A1 | * | 10/2004 | Besson | 382/131 |
| 2005/0243963 | A1 | * | 11/2005 | Ghelmansarai et al. | 378/7 |
| 2006/0008046 | A1 | * | 1/2006 | Ruhrnschopf | 378/7 |
| 2010/0316183 | A1 | * | 12/2010 | Fuchs et al. | 378/6 |

OTHER PUBLICATIONS

Kalendar, Monte Carlo calculations of x-ray scatter data for diagnostic radiology, Phys Med Biol, 1981, vol. 26, No. 5, pp. 835-849.*

* cited by examiner

*Primary Examiner* — Edward Glick
*Assistant Examiner* — Alexander H Taningco

(57) ABSTRACT

An imaging system and method for producing an image based on primary radiation. A separate image based solely on scattered radiation may also be obtained and may be of practical interests. The separation of primary and scattered radiation is achieved by utilizing a small beam exposure and a cone beam exposure, then the primary and scatter images are reconstructed based on a pencil beam model or from a Monte Carlo method. Other embodiments disclosed include two-layer detector arrays or volumetric detector arrays that measure the relationship between the dose and the position, from which the primary and scattered radiation can be extracted. In addition, by limiting a readout time of a detector, primary radiation component may be read because of a delay in the scattered radiation.

16 Claims, 6 Drawing Sheets

IMAGING SYSTEM AND METHOD UTILIZING PRIMARY RADIATION

The present application claims priority of U.S. Provisional Application No. 60/596,348, filed Sep. 19, 2005, the content of which is incorporated herein by reference in its entirety.

CROSS-REFERENCES TO RELATED APPLICATIONS

This application is a national stage of PCT/US2006/036550, filed Sep. 19, 2006.

BACKGROUND OF THE INVENTION

1. Field of the Invention

The invention relates generally to imaging systems and methods, and more particularly to imaging systems and methods for probing internal structures of an object.

2. Description of the Related Art

Radiations, such as X-ray, gamma rays, infrared and visible light, as well as mechanical waves such as sonic and ultrasonic waves have been used to probe internal structures of an object. Radiography, mammographic imaging, ultrasound, Computed Tomography (CT), Positron Emitting Tomography (PET), and Magnetic Resonance Imaging (MRI) have been used widely for medical diagnostic purposes as well as in industrial applications and security checks.

When a beam of radiation or wave interacts with an internal structure of an object, part of the beam is absorbed, and part scattered. The un-scattered portion of the beam, i.e., the primary radiation, traces accurately the attenuation coefficient of the internal structure.

Earlier generations of Computed Tomography (CT) use narrow beams or fan beams of X-rays, which suffer little from scattered X-ray photons. Newer generations of CT systems use cone-beam X-rays, with a field size in the order of 10 cm, and flat-panel detector arrays to reconstruct the attenuation map of a patient. Such a setup has certain advantages over traditional CTs that utilize narrow-beams or fan-beams in that the cone-beam CT is faster and may achieve a more uniform resolution in a 3-dimensional space.

However, due to the wide field at the target, cone-beam X-ray beams are associated with large amount of scattered radiations that tend to blur the reconstructed images, wherein the images are reconstructed based on the radiation absorbed by the detectors. The radiation absorbed by the detectors include both primary and scattered radiation. In the low-energy range (~100 kV) of X-ray photons involved in diagnostic imaging, the scatter-to-primary ratio (SPR) is on the order of 1, as compared to megavoltage X-rays, wherein typical SPR is on the order of 0.1 or smaller.

The necessity of separating primary and scattered radiation in cone-beam CTs has been noted (Jaffray, David A. et al., U.S. Patent Application Pub. No. 20030007601, "Cone-beam computerized tomography with a flat-panel imager"). It has been shown in measurements that scattered radiation may degrade the contrast-to-noise ratio (CNR) by a factor of 2 in a cone-beam CT images. There are also shading artifacts caused by scattered radiation. However, the benefits of volumetric (cone-beam) imaging warrant the effort to reduce scatter rather than going back to 2-D (fan-beam) or 1-D (pencil beam) imaging.

Swindell and Evans (Med. Phys., vol. 23, p. 63, 1996) had computed that the central axis SPR is almost linear with beam area, and is also almost linear with depth in water for a 6 MV beam. Bjarngard and Petti (Phys. Med. Biol. Vol. 33, p. 21, 1988) discovered that SPR(r,d), as a function of radius r and depth d, is a linear function of z:

$$SPR(r,d)=K\mu z, \qquad (1)$$

where $\mu$ is the linear attenuation coefficient for primary photons, and $z=rd/(r+d)$, and K is a coefficient that depends on the attenuation coefficient $\mu$. Nizin (Med. Phys. Vol. 18, p. 153) has used Eq. (1) to separate primary and scattered radiation in the case of a Co-60 beam in water.

Reducing scattered contamination has been achieved using grids in front of detectors. In an article "the influence of antiscatter grids on soft-tissue detectability in cone-beam computed tomography with flat-panel detectors" by Siewerdsen et al. (Med. Phys., vol. 31, p. 3506, 2004), it is demonstrated that this method filters out much of the scattered radiation based on the assumption that most of the scatter radiation is in directions different from those of primary photons. An analogous method of separating scattered radiation from primary radiation has been attempted over a thousand year ago, that is, an attempt to view stars in the daytime through a long tube. While some limited success has been achieved in this practice, its limitation is obvious in that the scattered day (solar) light usually still dominates the primary light from the stars even in the direction limited by the narrow tube.

Endo et al. (Med. Phys. Vol. 28, p. 469, 2001) studied the effect of scattered radiation on image noise in cone-beam CT, and the effectiveness of a focused collimator or a grid in reducing the noise.

BRIEF SUMMARY OF THE INVENTION

In one aspect, embodiments disclosed herein relate to reconstructing an image of an internal structure of an object based on a primary radiation component. In another aspect, embodiments disclosed herein relate to reconstructing an image of an internal structure of an object based on a scattered radiation component.

In another aspect, embodiments disclosed herein relate to reconstructing an image of an internal structure of an object based on separate primary and scattered radiation using mathematical means to separate the primary and the scattered radiation components. In another aspect, embodiments disclosed herein relate to modifying the configuration detector arrays to obtain information needed to separate primary and scattered radiation components.

In another aspect, embodiments disclosed herein relate to using two-layer detector arrays or 3-D volumetric detector arrays to detect a relationship between a radiation flux and a distance from a radiation source in order to obtain separate primary and scattered radiation components. In another aspect, embodiments disclosed herein relate to using a timing means to temporally distinguish primary radiation from scattered radiation.

In another aspect, embodiments disclosed herein relate to using pencil or fan beams together with cone beams to separate primary and scatter. In another aspect, embodiments disclosed herein relate to utilizing Monte Carlo simulations iteratively to produce separate images based on primary and scattered radiation, respectively.

DETAILED DESCRIPTION

Separating primary and scattered radiation in CT imaging has proved the usefulness of information conveyed by scattered photons in an X-ray inspection system (Mario, Arthur W. et al., U.S. Patent Application Pub. No. 20050089140, "Tomographic scanning X-ray inspection system using transmitted and Compton scattered radiation").

Mathematical means of separating primary and scattered radiation have been explored in the field of megavoltage X-ray radiation therapy as means to research the different properties and behaviors of the primary component and the scattered component (e.g., P. S. Nizin, "Electronic equilibrium and primary dose in collimated photon beams", Med. Phys., 20, 1721-1729 (1993); P. S. Nizin, "Geometrical aspects of scatter-to-primary ratio and primary dose", Med. Phys., vol. 18, p. 153, 1991). However, in the field of radiation therapy, such means are merely research tools in the case that Monte Carlo simulations are not accessible or computationally-non-viable, and cannot be applied to linear accelerators to physically separate the primary and the scatter components.

Figure 1:
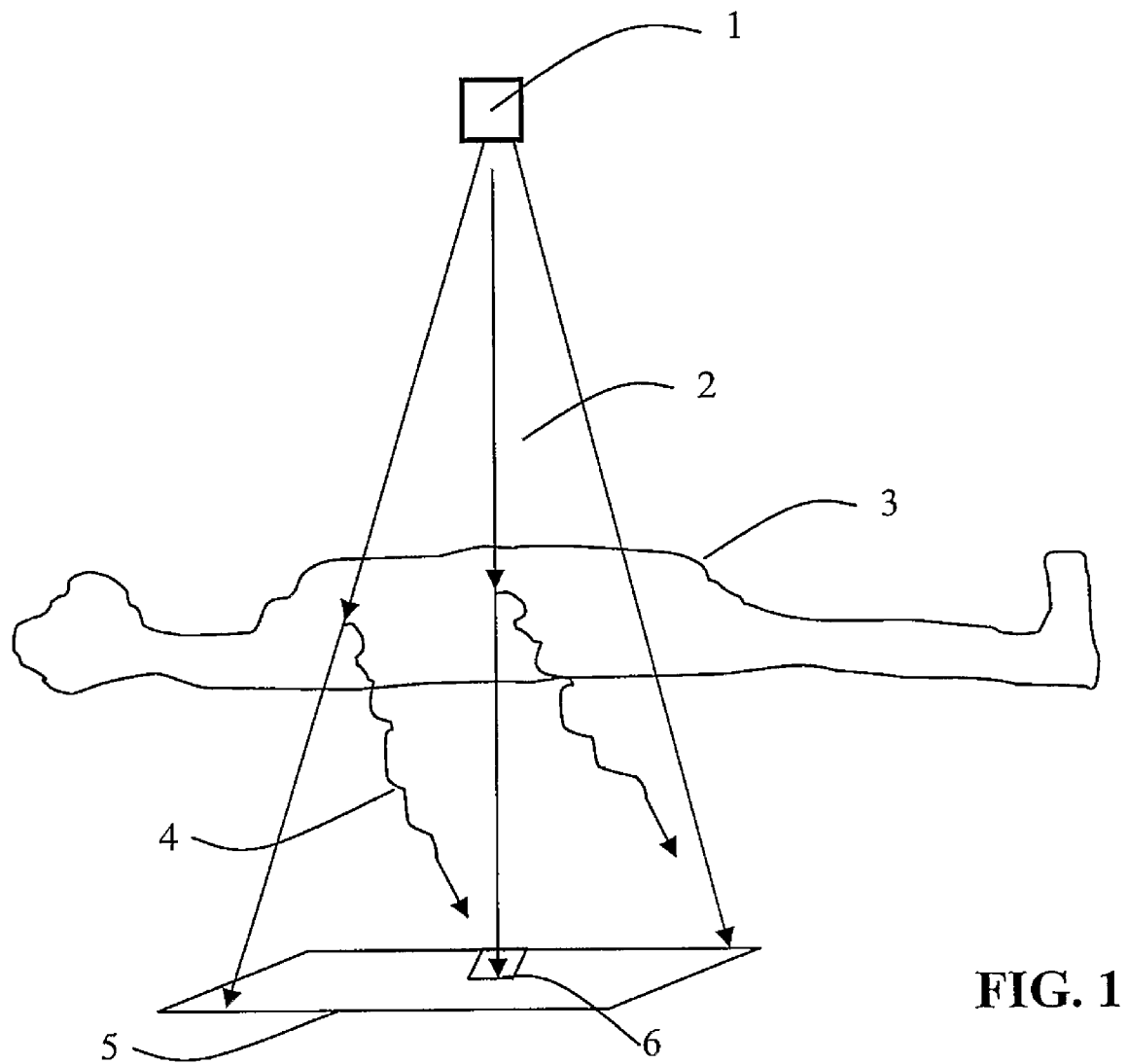
FIG. 1 illustrates the effect of scattered radiation.

Embodiments of the present invention are described in detail below with respect to the drawings. Like reference numbers are used to denote like parts throughout the figures. Referring to FIG. 1, in a typical CT system, X-ray source 1 emits a primary radiation beam 2, which passes through a patient 3 with attenuation and scattering taking place in the patient. Scattered radiation 4, traveling in the same direction or in a different direction from the primary radiation, reaches the flat panel detector array 5. A detector element 6 receives both the attenuated primary radiation and the scattered radiation. CT images reconstructed based on the readout from the detector element 6 is thus degraded due to the scattered radiation 4.

Figure 2:
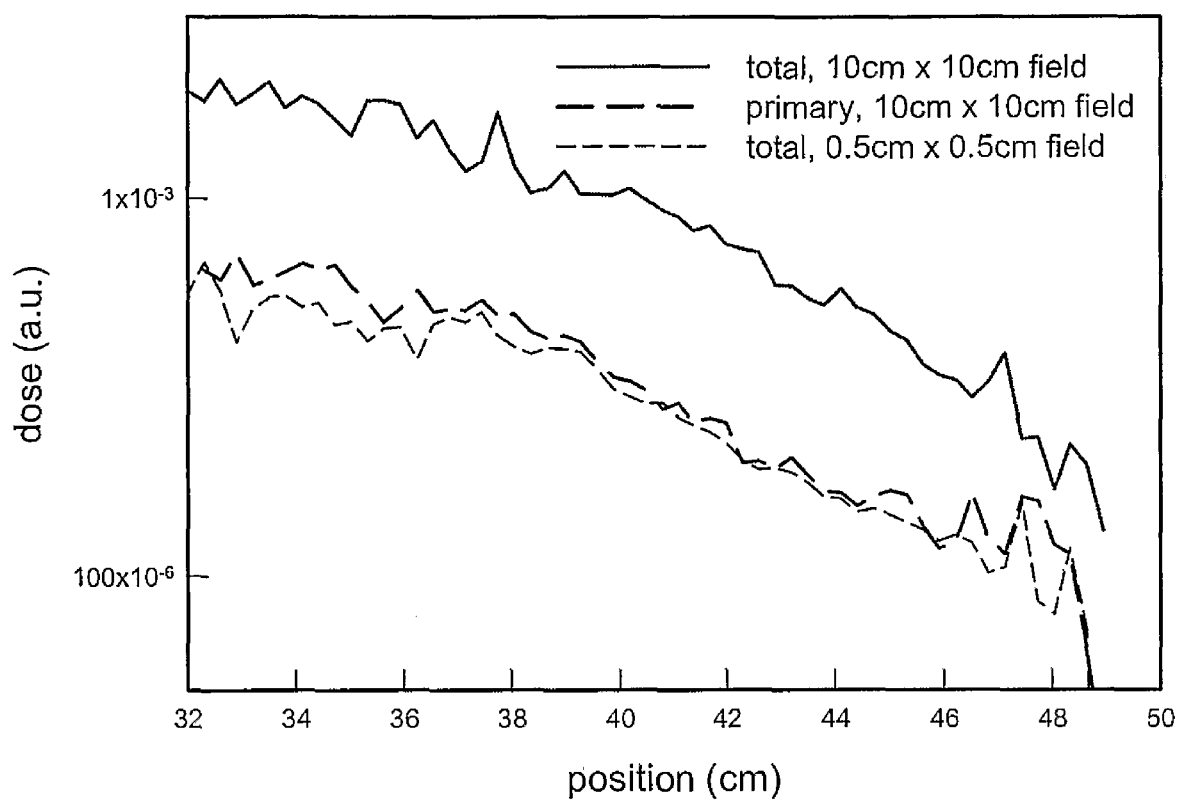
FIG. 2 illustrates that the total dose of a pencil (0.5 cm in width) X-ray beam in a patient follows closely the primary dose of a cone (10 cm) beam in the same patient toward the same direction.

Referring to FIG. 2, Monte Carlo simulation results for dose versus depth in a patient are shown for 140 kV X-ray beams through the patient. The total dose of a narrow (0.5 cm×0.5 cm) beam follows closely of the primary dose of a cone beam (10 cm×10 cm at a position of 40 cm inside the patient). Hence, the primary radiation of a cone beam can be simulated using a narrow beam. A simulation of a fan beam produces similar results, i.e., the scattered radiation in a fan beam is also very small.

Figure 3:
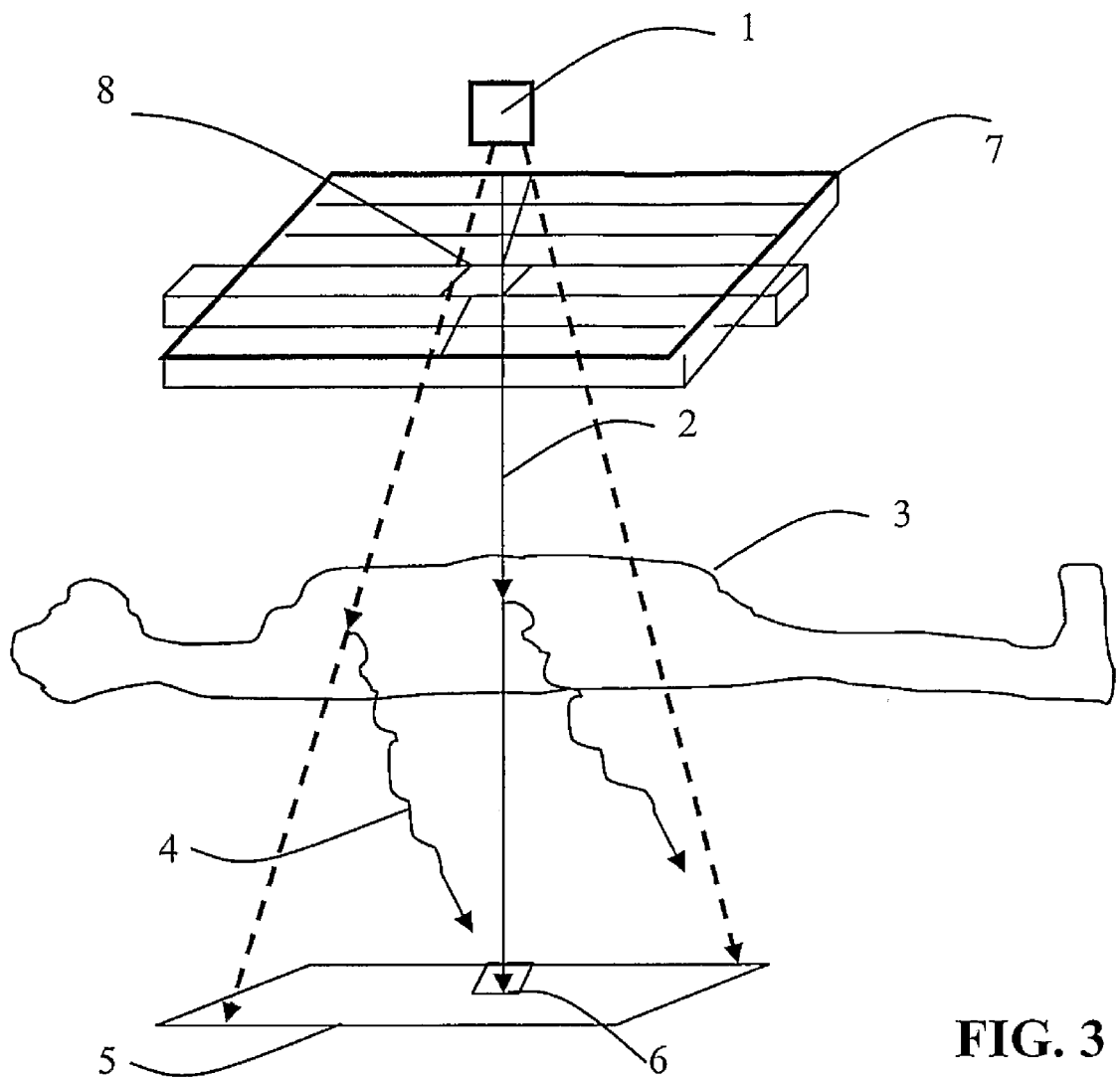
FIG. 3 shows an exemplary configuration of a CT system utilizing a pencil beam or a fan beam, together with a cone beam.

Based on the results described in FIG. 2, in accordance with some embodiments of the present invention, referring to FIG. 3, a multi-leaf collimator 7 is placed in front of the X-ray source 1. The collimator 7 has a variable opening 8, which is a small square hole, or a slit, or may have any other shapes as long as the opening 8 is smaller than the cone-beam itself.

In accordance with some embodiments of the present invention, narrow (<0.5 cm in diameter) X-ray beams are obtained using the above-mentioned collimator, and serve as probes to predict the primary component in the cone beam. A detector recording a dose in the direction of the cone beam sends the dose to a computer, which correct the dose to primary dose based on the knowledge from the narrow beams. The time spent on the narrow beams is not wasted, nor is the patient exposed more X-ray radiation without gaining the advantages of an improved image. In this configuration, signals from the narrow beams and the cone beams are used together, and the final signal-to-noise ratio (SNR) is still proportional to the total radiation exposure, including that from both the narrow beams and the cone beam.

Blocking means other than the multi-leaf collimator may be used to obtain the narrow and wide beams. For example, wedges, metal blocks or radiation source shutters may be used in place of, or together with the multi-leaf collimator 7. The narrow beam may be a pencil beam or a fan beam.

Detector elements other than the detector element 6 may also be turned "on" to detect the radiation scattered from the narrow beam away from the detector element 6. The scattered radiation may then be used to predict the strength of the scattering. Such information may be input to an image reconstruction algorithm.

In accordance with some embodiments of the present invention, a slit is used instead of the small hole. The slit effectively produces a fan beam, the dose of which is used to separate primary radiation of the cone beam. Again, all the signals recorded by the detectors are combined to make sure that the radiation or time is not wasted.

Those of ordinary skill in the art will recognize that, the above-mentioned embodiments can be effectively achieved using a combination of currently available fan-beam CT and cone-beam CT technology. That is, during scans the patient is exposed first to fan beams, then cone beams; or first to cone beams, then fan beams. The signals read off the detectors during the cone beam exposure are that of the total dose at the detectors, and such a total dose is separated into primary and scatter components based on detector read out during the fan beam exposure. The signals are combined, and the primary dose is used to reconstruct the CT images, and the scatter dose is used to reconstruct a separate set of CT images corresponding to scattered radiation.

Figure 4:
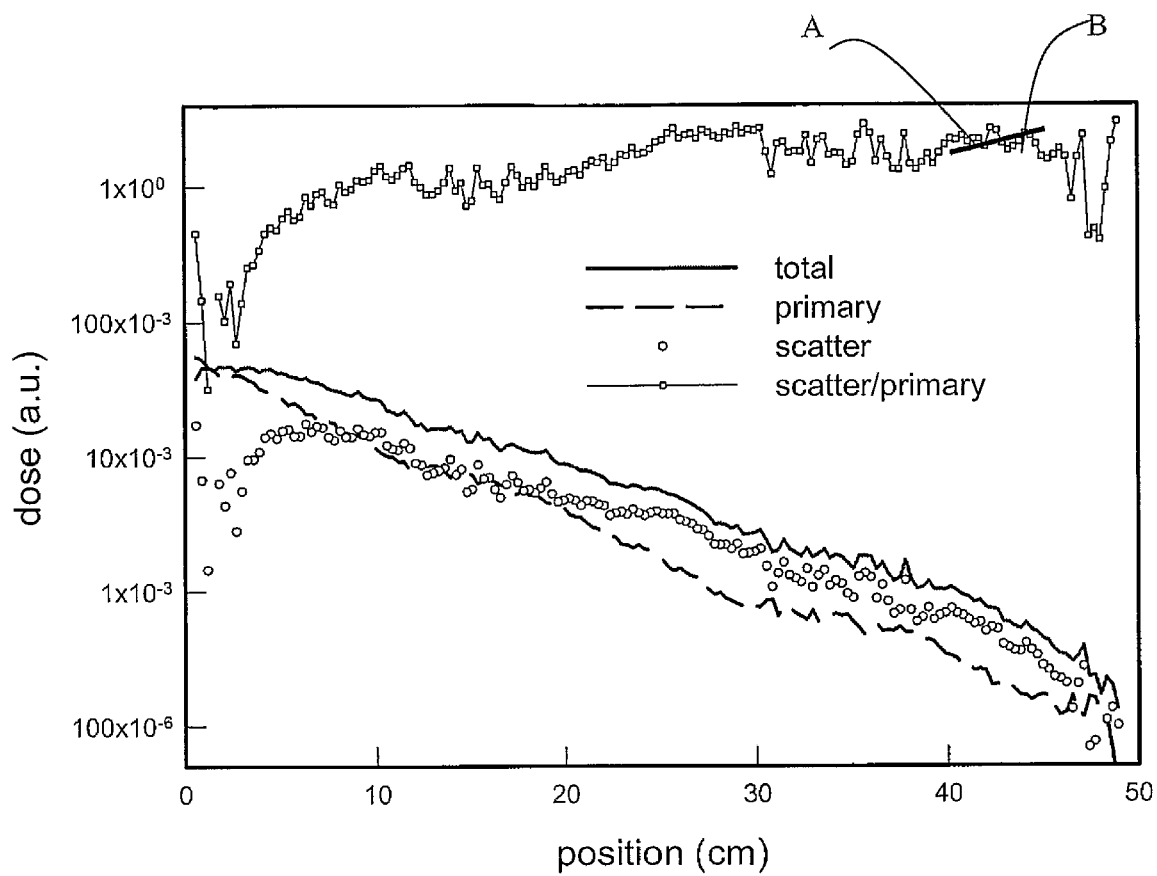
FIG. 4 demonstrates that the primary-to-scatter ratio is predictable over a longitudinal distance through a medium of known attenuations.

Referring to FIG. 4, the total dose of a cone beam inside an arbitrary geometry with a known attenuation map is shown. The primary and scattered dose are separated from the total dose, based on Equation (1). For example, if a detector is placed at a position A and another detector is placed at a position B, and if the attenuation properties of materials along the beam path between A and B are known, then based on Equation (1), the SPR can be derived. Using the read out of the total doses from point A and point B, separate primary and scatter doses can be derived based on the total doses and the SPR. This principle is applied to some embodiments of the present invention such as the one illustrated in FIG. 5.

Figure 5:
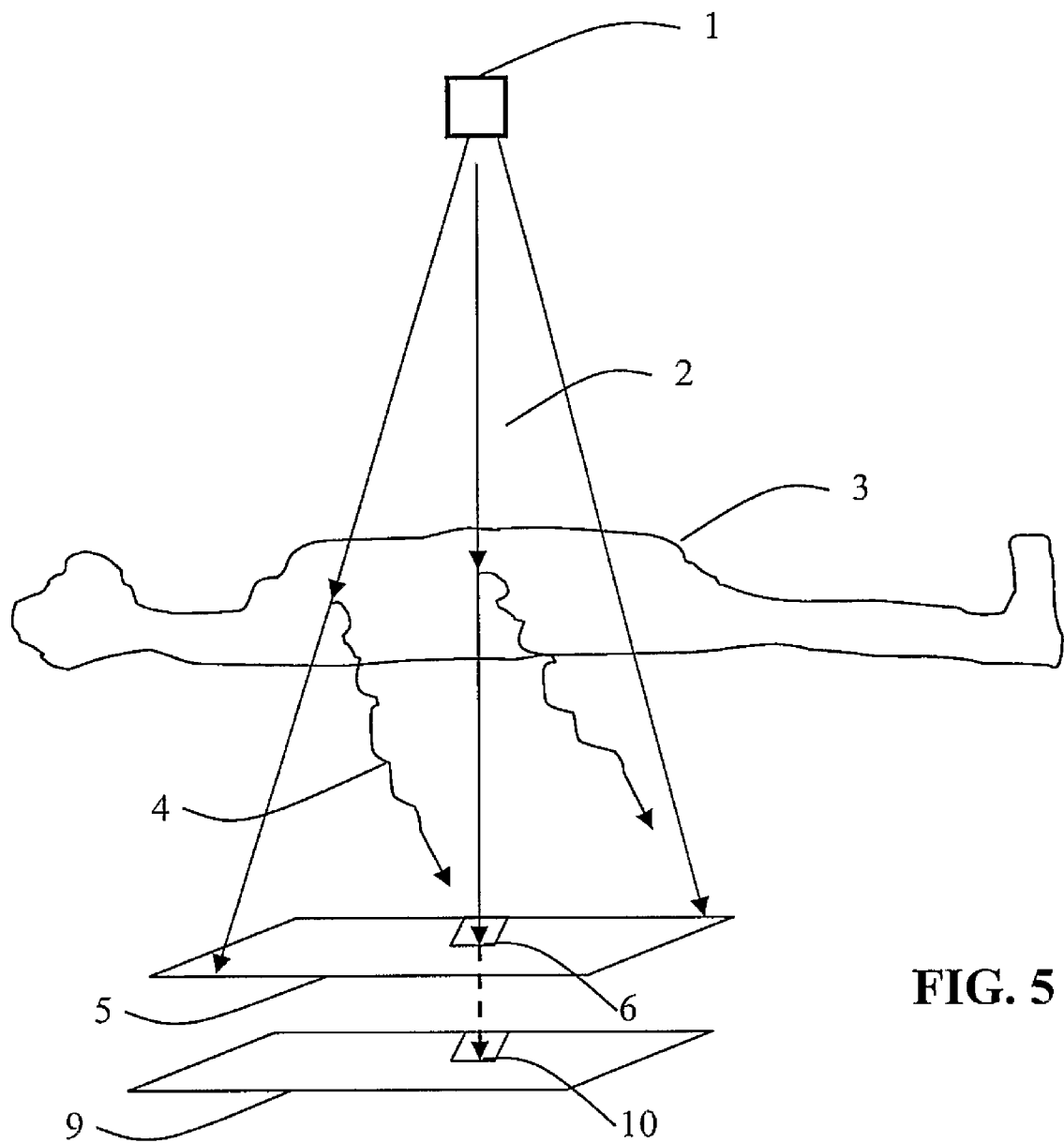
FIG. 5 illustrates the configuration of using two layers of flat panel X-ray detectors for the same cone beam.

Referring to FIG. 5, in accordance with some embodiments of the present invention, a conventional flat-panel X-ray detector array 5 may be supplemented with a second detector array 8. The detector system now includes two-layer detector arrays 5 and 9. The two flat panels 5 and 9 are separated by a known distance, and materials having known attenuation and scattering properties are filled in between the layers. The SPR, as a function of relative positions of detector element 6 and detector element 10, may be derived based on Monte Carlo simulations or analytical solutions such as Equation (1). The SPR depends on the known distance from the two layers, relative positions of detector elements, and the properties of the filling material. During a regular CT procedure, both layers record different dosages at the substantially same time, and a primary dose is derived based on the two dosages recorded by the two layers of detectors. The filling material between the two layers has known attenuation properties. Examples of such materials include, but are not limited to, air, water, plastic, solid water, rubber.

Those of ordinary skill in the art will recognize that, the effect of the two layers can alternatively be achieved using only one layer, such that its position is moved along the beam direction or against the beam direction from one exposure to another exposure. Such a recording of dose-distance relationship enables the separation of primary and scattered radiations based on algorithms described in Equation (1) and alike. Further, the motion of the detector array may be replaced with, or supplemented by moving the X-ray source 1.

Those of ordinary skill in the art will recognize that, the detector arrays can be alternatively implemented using volumetric detector arrays, which records dosage distribution in 3-D. The individual detector elements in the two-layer detector array, or in the volumetric detector arrays can be arranged such that they do not shadow each other in the beam. Alternatively if these detector elements do have shadows on the others, algorithms can be designed to take into account the detectors' attenuation coefficients, and the SPR can still be obtained. Detectors used in, for example, particle physics, track all the primary and scattered radiation and the knowledge learned therein may be applied to the imaging field based on the teachings of the present invention.

Those of ordinary skill in the art will also recognize that, an analytical equation other than Eq. (1) may be used as a mathematical means for separating the primary and scattered radiation. For example, it is well known that a primary radiation may follow an inverse-square law propagating, while a scattered radiation follow a different law in terms of a flux as a function of distance.

In accordance with some embodiments of the present invention, primary and scattered radiations are separated using timing means. The timing means may include coordinating the radiation emitting time and the detector turn-on and/or readout time to record primary photons because the scattered photons are delayed by the scattering events.

In accordance with some embodiments of the present invention, the CT images reconstructed from a conventional CT method are used as input for Monte Carlo simulations, which track all the transporting photons and label them as primary or scattered photons. The Monte Carlo simulations determine the fraction of primary and scattered components of the photons received by each detector, and a new set of images are reconstructed using only the primary component. The iterations can be repeated to obtain improved images.

After acquiring the primary images, scattered images can also be optionally obtained by comparing the primary with the total radiations. The set of primary images contain the most accurate density/attenuation information of the internal structure, and the set of scatter images may provide additional information of diagnostic interests. Being able to separate the scatter component from the primary component would make the finally-generated patient density map much more accurate, because the primary component responds to the density variation in a more predictable way, and the scattered component tend to degrade the image quality. By reconstructing the patient attenuation coefficient map based on primary radiation only, the density of tissues can be quantitatively analyzed from the re-constructed CT image.

The mathematical means to separate primary and scattered radiation are reduced to practice using computer algorithms, and such algorithms are constructed based on the properties and behaviors of the primary and scattered components of X-ray radiation. Said properties and behaviors of the primary and scattered components of may include, but are not limited to: (i) the primary component and the scattered component behave differently as the beam size increases. Such a property is known for megavoltage X-ray beams, where as the beam size increases, the percentage of the primary component relative to the total dose decreases; (ii) at small fields (<0.5 cm in diameter), all the dose deposited in tissues are almost exclusively primary dose. Such a property is useful, as demonstrated in the FIG. 2 of the present application, to separate the primary component from the scattered component of an X-ray radiation with an energy of 140 keV, typical for the diagnostic imaging purposes; (iii) the primary component and the scattered component behave differently as the distance from the X-ray source increases. Such a behavior is known for radiation at many different wavelengths. In the case of diagnostic X-ray, Equation (1) quantitatively represents one of such behaviors; (iv) the primary component and the scattered component react differently to tissue density variations when transporting through the patient tissue. Such different behaviors are described implicitly in equations dominating Monte Carlo simulations of radiation transport, where each individual photons are followed and the primary and scattered components are labeled within Monte Carlo simulations and the final simulation results are connected to the measured quantities; (v) scattering events take a short time to occur, while primary photons reach the detectors only after a propagation delay.

Figure 6:
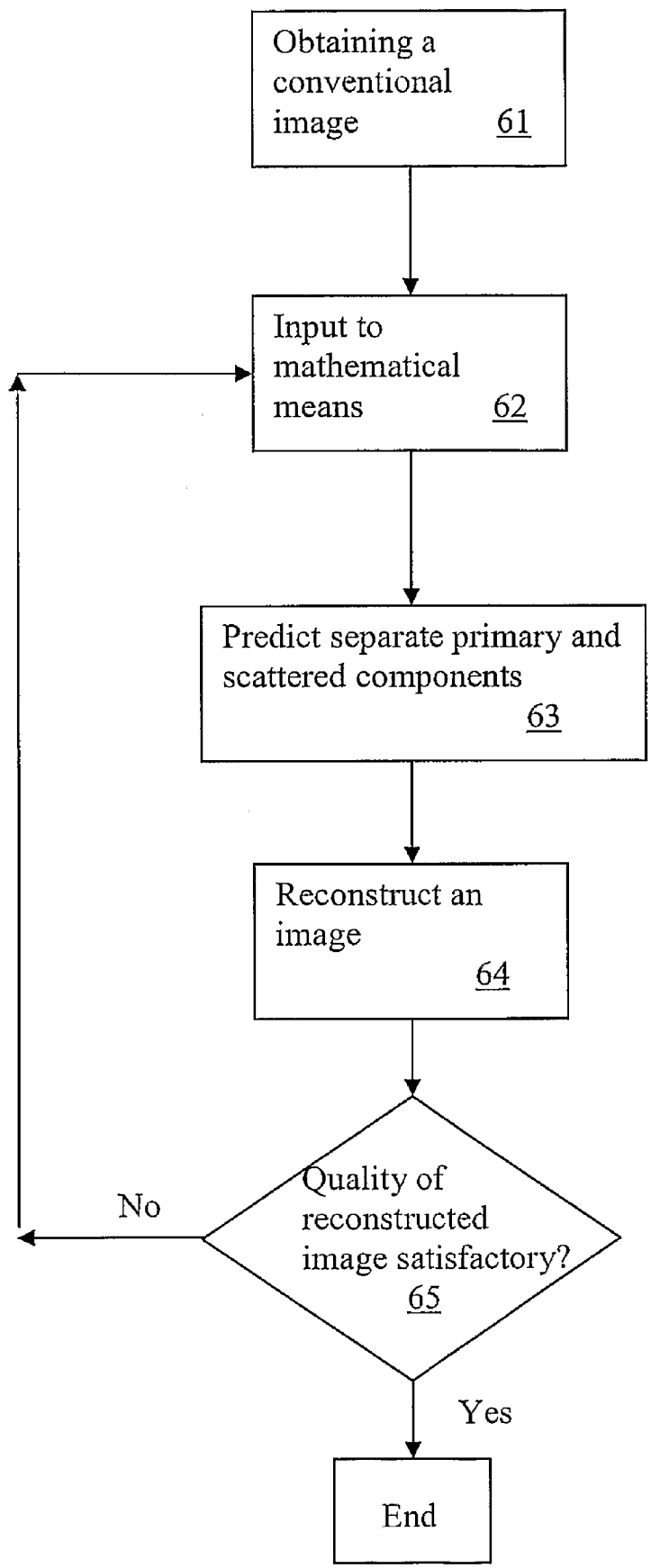
FIG. 6 shows a method of improving an image quality by iterating image reconstruction processes.

A method of obtaining an improved CT image in accordance with some embodiments of the present invention is summarized in FIG. 6. A conventional image, without separating the primary and scattered radiation components, may be first obtained in the step 61. The conventional image is inputted to a mathematical means in the step 62. The mathematical means may include an analytical equation similar to Equation (1), or may include a Monte Carlo algorithm. Using the mathematical means, a partial separation of primary and scattered radiation components is achieved in the step 63. An image may subsequently reconstructed based on the partial separation in the step 64. If the quality of the reconstructed image is deemed unsatisfactory in the step 65, the reconstructed image may be inputted back to the mathematical means and the steps reiterated starting with the step 62. Otherwise, the reconstructed image is outputted for use. A separate image constructed based solely on the scattered radiation may be optionally generated as the scattered radiation may also contain useful information.

The methods in the present invention may be implemented in a computer readable medium.

While the invention has been described with respect to a limited number of embodiments, those skilled in the art, having benefit of this disclosure, will appreciate that other embodiments can be advised and achieved which do not depart from the scope of the invention as disclosed herein. Accordingly, the scope of the invention should be limited only by the attached claims.

What is claimed is:

1. An imaging system configured to construct a Computed Tomography (CT) image of an internal structure of an object based on a primary radiation, wherein the imaging system is configured to separate the primary radiation from a scattered radiation based on a mathematical model, the imaging system comprising:

a computer configured to calculate a scatter-to-primary ratio (SPR) based on the mathematical model to thereby:

separate of the primary radiation from the scattered radiation using the SPR in the mathematical model; and construct a CT image based on the primary radiation derived from the mathematical model, wherein the mathematical model is built upon that the primary radiation propagates in a way different from the scattered radiation; and a detector configured to detect radiation intensities in a first position and in a second position, wherein the detector comprises two layers of flat-panel X-ray detector arrays disposed respectively at the first position and the second position and configured to measure a decreasing radiation flux versus distance.

2. The imaging system of claim 1, wherein the mathematical model comprises at least one of a Monte Carlo algorithm, or an analytical pencil beam model that uses a narrow beam to predict the primary radiation of a wide-beam X-ray radiation.

3. The imaging system of claim 1, wherein the mathematical model includes a description of $SPR(r,d) = K\mu z$, where r is a radius, d is a depth, $\mu$ is a linear attenuation coefficient for primary photons, $z = rd/(r+d)$, and K is a coefficient that depends on $\mu$.

4. The imaging system of claim 1, wherein the mathematical model is characterized in that the primary radiation has a decreasing flux versus distance as governed by an inverse-squared law.

5. The imaging system of claim 1, wherein a space between the two layers of flat-panel X-ray detector arrays is filled with a material with specified properties.

6. The imaging system of claim 5, wherein the material comprises at least one of air, water, solid water, plastic, or rubber.

7. The imaging system of claim 1, wherein the mathematical model is configured to use iteration of an output CT image as an input density map to Monte Carlo simulations, to generate a more accurate density map image.

8. The imaging system of claim 1, wherein the detector comprises a is configured as a two-layer detector array.

9. The imaging system of claim 1, wherein the detector comprises a 3-dimensional volumetric detector array including the two layers.

10. The imaging system of claim 1, wherein at least a portion of the detector is configured to move along the direction of the primary radiation.

11. The imaging system of claim 1, further comprising a timing device configured to turn on a detecting element for a short period such that the detecting element detects only primary radiation.

12. The imaging system of claim 1, wherein the detector is configured to selectively read an output from a first selected detecting element to obtain a primary radiation reading and a second selected detecting element to obtain a scattered radiation reading.

13. The imaging system of claim 1, wherein the imaging system is further configured to generate a CT image based on the scattered radiation.

14. The imaging system of claim 1, further comprising a blocking device including a multi-leaf collimator.

15. The imaging system of claim 14, wherein the multi-leaf collimator is configured to generate both a narrow beam and a wide beam, and wherein the narrow beam comprises at least one of a pencil beam or a fan beam, and wherein the wide beam comprises a cone beam.

16. A non-transitory computer-readable medium having instructions stored thereon and configured to construct Computed Tomography (CT) images from data obtained from a CT system, wherein the CT system comprises a radiation source configured to transmit a cone-beam of X-rays, and a detection system including at least two detecting elements located at different distances from the radiation source and configured to measure X-ray radiation doses at different distances, the instructions comprising:

deriving, from the measured X-ray radiation doses and using a mathematical model, a scatter-to-primary ratio (SPR) of the X-ray radiation doses as a function of position;

separating primary and scattered components of the measured X-ray radiation doses based on the derived SPR;

constructing a first set of CT images with the primary component; and constructing a second set of CT images with the scattered component.

* * * * *